US006774139B1

(12) United States Patent
Uckun et al.

(10) Patent No.: US 6,774,139 B1
(45) Date of Patent: Aug. 10, 2004

(54) DUAL FUNCTION MICROBICIDES

(75) Inventors: Fatih M. Uckun, White Bear Lake, MN (US); Osmond D'Cruz, Vadnais Heights, MN (US)

(73) Assignee: Parker Hughes Institute, Roseville, MN (US)

( * ) Notice: Subject to any disclaimer, the term of this patent is extended or adjusted under 35 U.S.C. 154(b) by 207 days.

(21) Appl. No.: 09/608,710

(22) Filed: Jun. 30, 2000

(51) Int. Cl.[7] .................. A61K 31/44; A61K 31/47; A61K 7/00; A01N 25/00
(52) U.S. Cl. .................. 514/353; 514/318; 514/332; 514/841; 514/843; 424/401
(58) Field of Search .................. 514/353, 310, 514/841, 843, 318, 332; 424/401

(56) References Cited

U.S. PATENT DOCUMENTS

| | | | | |
|---|---|---|---|---|
| 5,593,993 | A | * | 1/1997 | Morin et al. .................. 514/247 |
| 5,658,907 | A | * | 8/1997 | Morin et al. .................. 514/247 |

FOREIGN PATENT DOCUMENTS

| | | |
|---|---|---|
| EP | 0 540 143 A2 A3 | 5/1993 |

OTHER PUBLICATIONS

Uckun et al. "N–[2–(1–cyclohexenyl)ethyl]–N'–[2–(5–bromopyridyl)]–thiourea and N'–[2–(1–cyclohexenyl)ethyl]–N'–[2–(5–chloropyridyl)]–thiourea as potent inhibitors of multidrug–resistant human immunodeficiency virus–1," 1999, Bioorganic & Medicinal Chemistry Letters, vol. 9, pp. 2721–2726.*

D'Cruz, Osmond J. et al., "Novel Thiourea Compounds as Dual–Function Microbicides," *Biology of Reproduction*, 63:196–205 (2000). Jun. 19.

Ahgren C, Backro K, Bell FW, Cantrell AS, Clemens M, Colacino JM, Deeter JB, Engelhardt JA, Jaskunas HM, Johansson NG, Jordan CL, Kasher JS, Kinnick MD, Lind P, Lopez C, Morin JMJ, Muesing MA, Noreen R, Oberg B, Paget CJ, Palkowitz JA, Parrish CA, Pranc P, Rippy MK, Rydergard C, Sahlberg C, Swanson S, Ternansky RJ, Unge T, Vasileff RT, Vrang L, West SJ, Zhang H, Zhou XX. "The PETT series, a new class of potent nonnulceoside inhibitors of human immunodeficiency virus type 1 reverse transcriptase", *Antimicrob Agents Chemother*, vol. 39, pp. 1329–1335 (1995).

Baba M, Shigeta S, Tanaka H, Miyasaka T, Ubasawa M, Umezu K, Walker RT, Pauwels R, De Clercq E. "Highly potent and selective inhibition of HIV–1 replication by 6–phenylthiouracil derivatives", *Antiviral Res*, vol. 17, pp. 245–264 (1992).

Baccetti B, Benedetto A, Burrini AG, Collodel G, Ceccarini C, Crisa E, DiCaro A, Garbuglia AR, Massacesi A, Piomboni P, Solazzo D. "HIV–1 particles in spermatozoa of patients with AIDS and their transfer into the oocytes", *J Cell Biol*, vol. 127, pp. 903–914 (1994).

Balzarini J, Perez MJ, San Felix A, Schols D, Perno CF, Vandamme AM, Camarasa MJ, De Clercq E. "2',5'–Bis–O–(tert–butyldimethylsilyl)–3'–spiro–5"–(4"–amino–1",2"–oxathiole–2",2'–dioxide)pyrimidine (TSAO) nucleoside analogues: highly selective inhibitors of human immunodeficiency virus type 1 that are targeted at the viral reverse transcriptase", *Proc Natl Acad Sci U S A*, vol. 89, pp. 4392–4396 (1992).

(List continued on next page.)

*Primary Examiner*—Shengjun Wang
(74) *Attorney, Agent, or Firm*—Merchant & Gould P.C.

(57) ABSTRACT

Contraceptive activity as well as anti-microbial, particularly anti-viral protection is provided by contraceptive compositions containing a thiourea compound of the invention exhibiting spermicidal or sperm-immobilizing activity. Preferred compounds of the invention are cyclohexenyl-substituted thiourea compounds.

7 Claims, 1 Drawing Sheet

OTHER PUBLICATIONS

Bell FW, Cantrell AS, Hogberg M, Jaskunas SR, Johansson NG, Jordan CL, Kinnick MD, Lind P, Morin JM, Jr, Noreen R, Oberg B, Palkowitz JA, Parrish CA, Pramo P, Sahlberg C, Ternansky RT, Vasileff RT, Vrang L, West SJ, Zhang H, Zhou XX. "Phenethylthiazolethiourea (PETT) compounds, a new class of HIV–1 reverse transcriptase inhibitors. I. Synthesis and basic structure–activity relationship studies of PETT analogs", *J Med Chem* vol. 38, pp. 4929–4936 (1995).

Bosworth N, Towers P. "Scintillation proximity assay", *Nature*, vol. 341, pp. 167–168 (1989).

Cantrell AS, Engelhardt P, Hogberg M, Jaskunas SR, Johansson NG, Jordan CL, Kangasmetsa J, Kinnick MD, Lind P, Morin JM, Jr, Muesing MA, Noreen R, Oberg B, Pranc P, Sahlberg C, Ternansky RJ, Vasileff RT, Vrang L, West SJ, Zhang H. "Phenethylthiazolylthiourea (PETT) compounds as a new class of HIV–1 reverse transcriptase inhibitors. 2. Synthesis and further structure–activity relationship studies of PETT analogs", *J Med Chem*, vol. 39, pp. 4261–4274 (1996).

"CDCP Update: US HIV and AIDS cases reported through Dec. 1996", *HIV/AIDS Surveillance Report*, vol. 8, pp. 8:1–33 (1997).

Celum CL, Watts DH. "HIV and Women" *In: Spach DL, Hooton RM (eds.) The HIV manual. New York: Oxford University Press*, pp. 120–127 (1996).

Chantler E. "Vaginal spermicides: some current concerns", *British Family Planning*, vol. 17, pp. 17:118–119 (1992).

Cook RL, Rosenberg MJ. "Do spermicides containing nonoxynol–9 prevent sexually transmitted infections?", *Sex Transm Dis*, vol. 25, pp. 144–150 (1998).

Cookson C. "WHO to concentrate HIV strategy on vaginal microbicide", *Br Med J*, vol. 307, pp. 1375–1376 (1993).

D'Cruz OJ, Ghosh P, Uckun FM. "Spermicidal activity of metallocene complexes containing vanadium(IV) in humans", *Biol Reprod*, vol. 58, pp. 1515–1526 (1998).

D'Cruz OJ, Uckun FM. "Novel derivatives of phenethyl–5–bromopyridylthiourea and dihydroalkoxybenzyloxopyrimidine are dual–function spermicides with potent anti–human immunodeficiency virus activity"*Biol Reprod*, vol. 60, pp. 1419–1428 (1999).

Danel K, Larsen E, Pedersen EB, Vestergaard BF, Nielsen C. "Synthesis and potent anti–HIV–1 activity of novel 6–benzyluracil analogues of 1–[(2–hydroxyethoxy)methyl] –6–(phenylthio)thymine", *J Med Chem*, vol. 39, pp. 2427–2431 (1996).

Danel K, Pedersen EB, Nielsen C. "Synthesis and anti–HIV–1 activity of novel 2,3–dihydro–7H–thiazolo[3,2–a] pyrimidin–ones", *J Med Chem*, vol. 41, pp. 191–198 (1998).

De Clercq E. "Inhibitors targeted at the reverse transcriptase" *J Acquired Immune Defic Syndr Res Human Retrovirus*, vol. 8, pp. 119–134 (1988).

Ding J, Das K, Moereels H, Koymans L, Andries K, Jansen PA, Hughes SH, Arnold E. "Structure of HIV–1 RT/TIBO R 86163 complex reveals similarity in the binding of diverse nonnucleoside inhibitors", *Nat Struct Biol*, vol. 2, pp. 407–415 (1995).

Ding J, Das K, Tantillo C, Zhang W, Clark Jr, AD, Jessen S, Lu X, Hsiou Y, Jacobo–Molina A, Andries K, Pauwels R, Moereels H, Koymans L, Janssen PAJ, Smith RHJ, Kroeger–Koepke R, Michejda CJ, Hughes SH, Arnold E. "Structure of HIVl–1 reverse transcriptase in a complex with the nonnucleoside inhibitor alpha–APA R 95845 at 2.8 A resolution", *Structure*, vol. 3, pp. 365–379 (1995).

Erice A, Lieler CL, Meyers DE, Sannerund KJ, Irvin JD, Balfour HH, Uckun FM. "Inhibition of zidovudine (AZT)–sensitive strains of human immunodeficiency virus type 1 by pokeweed antiviral protein targeted to CD4+ cells", *Antimicrob Agents Chemother*, vol. 37, pp. 835–838 (1993).

Greene WC. "The molecular biology of human immunodeficiency virus type 1 infections", *N Engl J Med*, vol. 324, pp. 324:308–317 (1991).

Heinisch G, Matuszczak B, Pachler S, Rakowitz D. "The inhibitory activity of diazinyl–substituted thiourea derivatives on human immunodeficiency virus type 1 reverse transcriptase", *Antivir Chem Chemother*, vol. 8, pp. 443–446 (1997).

Hira SK, Feldblum PJ, Kamanga J, Mukelabai G, Weir SS, Thomas JC. "Condom and nonoxynol–9 use and the incidence of HIV infection in serodiscordant couples in Zambia", *Int J STD AIDS*, vol. 8, pp. 243–250 (1997).

Hogberg M, Sahlberg C, Engelhardt P, Noreen R, Kangasmetsa J, Johansson NG, Oberg B, Vrang L, Sahlberg BL, Unger T, Logren S, Fridborg K, Backbro K. "Urea–PETT compounds as a new class of HIV–reverse transcriptase inhibitors. 3. Synthesis and further structure–activity relationship studies of PETT analogues", *J Med Chem*, vol. 42, pp. 4150–4160 (1999).

Hooten TM, Hillier S, Johnson C, Roberts PL, Stamm WE. "*Eschericia coli* bacteriuria and contraceptive method", *JAMA*, vol. 265, pp. 64–69 (1991).

Hsiou Y, Das K, Ding J, Clark AD Jr, Kleim JP, Rosner M, Winkler I, Riess G, Hughes SH, Arnold E. "Structure of tyr188Leu mutant and wild–type HIV–1 reverse transcriptase complexed with the non–nucleoside inhibor HBY 097: inhibitor flexibility in a useful design feature for reducing drug resistance", *J Mol Biol*, vol. 284, pp. 313–323 (1998).

Kohlstaedt LA, Wang J, Friedman JM, Rice PA, Steitz TA. "Crystal structure at 3.5 A resolution of HIV–1 reverse transcriptase complexed with an inhibitor", *Science*, vol. 256, pp. 1783–1790 (1992).

Kreiss J, Ngugi E, Holmes K, Ndinya AJ, Waiyaki P, Roberts PL, Ruminjo I, Ajabi R, Kimata J, Fleming TR, Anzala A, Holton D, Plummer F. "Efficacy of nonoxynol–9 contraceptive sponge use in preventing heterosexual transmission of HIV in Nairobi prostitutes", *JAMA*, vol. 268, pp. 477–482 (1998).

Lange JMA, Karam M, Plot P. "Boost for vaginal microbicides against HIV", *Lancet*, vol. 341, pp. 1356–1359 (1993).

Mai A, Artica M, Sbardella G, Quartarone S, Massa S, Loi AG, Montis AD, Scintu F, Putzolu M, La Colla P. "Dihydro(alkythio)(naphthylmethyl)oxopyrimidines: Novel non–nucleoside reverse transcriptase inhibitors of the S–DABO series", *Med Chem*, vol. 40, pp. 40:1447–1454 (1997).

Mann J, Tarantola D. "The global AIDS pandemic" *In: Velji AM (ed.), Infectious Disease Clinics of North America. Philadelphia: Saunders*; pp. 275–285 (1995).

Mao C, Vig R, Venkatachalam TK, Sudbeck EA, Uckun FM. "Structure–based design of N–[2–(1–piperidinylethyl)]–N [2–(5–bromopyridyl)]–thiourea and N–[2–(1–piperzainyl-ethyl)]–N'–[2–(5–bromopyridyl)thiourea as potent non–nucleoside inhibitors of HIV–1 reverse transcriptase", *Bioorg Med Chem Lett*, vol. 8, pp. 2213–2218 (1998).

Mati JK, Hunter DF, Maggwa BN, Tukei PM. "Contraceptive use and the risk of HIV infection in Nairobi, Kenya", *Int J Obstet Gynecol*, vol. 48, pp. 61–67 (1995).

McGroarty JA, Chong S, Reid G, Bruce AW. "Influence of the spermicidal compound nonoxynol–9 on the growth and adhesion of urogenital bacterial in vitro", *Curr Microbiol*, vol. 21, pp. 219–223 (1990).

Mitsuya H, Yarchoan R, Broder S. "Molecular targets for AIDS therapy", *Science*, vol. 249, pp. 1533–1544 (1990).

Niruthisard SR, Roddy E, Chutivongse S. "The effects of frequent nonoxynol–9 use on the vaginal and cervical mucosa", *Sex Transm Dis*, vol. 18, pp. 176–179 (1991).

Osborn JE. "Women and HIV/AIDS: the silent epidemic", *Sex Info Educ Council US Rep*, vol. 19, pp. 1–4 (1991).

OTC Panel. "Vaginal contraceptive drug products for over-the counter human use", *Federal Register*, vol. 45, pp. 82014–82049 (1980).

Pauwels R, Andries K, Desmyter J, Schols D, Kukla MJ, Breslin HJ, Raeymaeckers A, Van Gelder J, Woestenborghs R, Heykants J, Schellekens K, Janssen MAC, De Clercq E, Jansssen PA. "Potent and selective inhibition of HIV–1 replication in vitro by a novel series of TIBO derivatives", *Nature*, vol. 343, pp. 470–474 (1990).

Pontikis R, Benhida R, Aubertin AM, Grierson, DS, Monneret C. "Synthesis and anti–HIV activity of novel N–1 side chain–modified analogs of 1–[(2–hydroxyethoxy)methyl]–6–(phenylthio)thymine (HEPT)", *J Med Chem*, vol. 40, pp. 1845–1854 (1997).

Potts M. "The urgent need for a vaginal microbicide in the prevention of HIV transmission", [*Editorial*] *Am J Public Health*, vol. 84, pp. 890–891 (1994).

Quayle AJ, Xu C, Mayer KH, Anderson DJ. "T lymphocytes and macrophages, but not motile spermatozoa, are a significant source of human immunodeficiency virus in semen", *J Infect Dis*, vol. 176, pp. 960–968 (1997).

Quinn TC. "Global burden of the HIV pandemic", *Lancet*, vol. 348, pp. 348:99–106 (1996).

Rekart ML. "The toxicity and local effects of the spermicide nonoxynol–9", *J Acquir Immune Defic Syndr*, vol. 5, pp. 425–427 (1992).

Ren J, Esnouf R, Garman E, Somers D, Ross C, Kirby I, Keeling J, Darby G, Jones Y, Stuart D, Stammers D. "High resolution structures of HIV–1 RT from four RT–inhibitor complexes", *Nat Struct Biol*, vol. 2, pp. 293–302 (1995).

Ren J, Esnouf R, Hopkins A, Ross C, Jones Y, Stammers D, Stuart D. "The structure of HIV–1 reverse transcriptase complexed with 9–chloro–TIBO: lessons for inhibitor design", *Structure*, vol. 3, pp. 915–926 (1995).

Roddy RE, Cordero M, Cordero C, Fortney JA. "A dosing of nonoxynol–9 and genital irritaion", *Int J STD & HIV*, vol. 4, pp. 165–170 (1993).

Roddy RE, Zeking L, Ryan KA, Tamoufe U, Weir SS, Wong EL. "A controlled trial of nonoxynol–9 film to reduce male–to–female transmission of sexually transmitted diseases", *N Engl J Med*, vol. 339, pp. 504–510 (1998).

Romero DL, Morge, RA, Genin MJ, Biles C, Busso M, Resnick L, Althaus IW, Reusser F, Thomas RC, Tarpley WG. "Bis(heteroaryl)piperazine (BHAP) reverse transcriptase inhibitors: structure–activity relationships of novel substituted indole analogues and the identification of 1–[(5–methanesulfonamido–1H–indol–2–yl)–carbonyl]–4–[3–[(1–methylethyl)amino]–pyridinyl]piperazine monomethanesulfonate (U–90152S), a second–generation clinical candidate", *J Med Chem*, vol. 36, pp. 1505–1508 (1993).

Rosenstein IJ, Stafford MK, Kitchen VS, Ward H, Weber JN, Taylor–Robinson D. "Effect of normal vaginal flora of three intravaginal microbicidal agents potentially active against human immunodeficiency virus type 1",*J, Infect Dis*, vol. 177, pp. 1386–1390 (1998).

Smerdon SJ, Jager J, Wang J, Kohlstaedt LA, Chirino AJ, Friedman JM, Rice PA, Steitz TA. "Structure of the binding site for nonnucleoside inhibitors of the reverse transcriptase of human immunodeficiency virus type 1", *Proc Natl Acad Sci U S A*, vol. 91, pp. 3911–3915 (1994).

Stafford MK, Ward H, Flanagan A, Rosenstein IJ, Taylor–Robinson D, Smith JR, Weber J, Kitchen VS. "A safety of nonoxynol–9 as a vaginal microbicide: evidence of adverse effects",*J Acquir Immune Defic Syndr Hum Retrovirol*, vol. 17, pp. 327–331 (1998).

Tanaka H, Baba M, Hayakawa H, Sakamaki T, Miyasaka T, Ubasawa M, Takashima H, Sekiya K, Nitta I, Shigeta S, Walker RT, Balzarini J, De Clercq E. "A new class of HIV–1–specific 6–substituted acyclouridine derivatives: synthesis and anti–HIV–1 activity of 5– or 6–substituted analogues of 1–[(2–hydroxyethoxy)methyl]–6–(phenylthio) thymine (HEPT)", *J Med Chem*, vol. 34, pp. 349–357 (1991).

Tryphonas L, Buttar HS. "Morphological evidence for vaginal toxicity of Delfan contraceptive cream in the rat", *Toxicol Lett*, vol. 20, pp. 289–295 (1984).

Uckun FM, Chelstrom LM, Ahlgren–Tuel L. Dibirdik I, Irvin JD, Langlie M–C, Myers DE. "TXU (Anti–CD7)–pokeweed antiviral protein as a potent inhibitor of human immunodeficiency virus", *Antimicrob Agents Chemother*, vol. 42, pp. 383–388 (1998).

Uckun FM, D'Cruz OJ. "Prophylactic contraceptives for HIV/AIDS", *Hum Reprod Update*, vol. 5, pp. 506–514 (1999).

Uckun FM, Mao C, Pendergrass S, Maher D, Zhu D, Tuel–Ahlgren L, Venkatachalam TK. "N–[2–(1–cyclohexenyl)ethyl)]–N'–[2–(5–bromopyridyl)]–thiourea and N–[2–(1–cyclohexenyl)ethyl]–N'–[2–(5–chloropyridyl)]–thiourea as potent inhibitors of multidrug–resistant human immunodeficiency virus–1", *Bioorg Med Chem Lett*, vol. 9, pp. 2721–2726 (1999).

Vig R, Mao C, Venkatachalam TK, Tuel–Ahlgren L, Sudbeck E, Uckun FM. "Rational design and synthesis of phenethyl–5–bromopyridyl thiourea derivatives as potent non–nucleoside inhibitors of HIV reverse transcriptase", *Bioorg Med Chem*, vol. 6, pp. 1789–1797 (1998).

Weir SS, Roddy RE, Zekeng L, Feldblum PJ. "Nonoxynol–9 use, genital ulcers, and HIV infection in a cohort of sex workers", *Genitourin Med*, vol. 71, pp. 78–81 (1995).

Wright TC Jr, Ellerbrock TV, Chiasson MA, Van Devanter N, Sun XW. "Cervical intraepithelial neoplasia in women infected with human immunodeficiency virus: prevalence, risk factors, and validity of Papanicolaou smears: New York Cervical Disease Study", *Obstet Gynecol*, vol. 84, pp. 591–597 (1994).

Zarling JM, Moran PA, Haffar O, Sias J, Richman DD, Spina CA, Myers DE, Kuebelbeck V, Ledbetter JA, Uckun FM. "Inhibition of HIV replication by pokeweed antiviral protein targeted to CD4+ cells by monoclonal antibodies", *Nature*, vol. 347, pp. 92–95 (1990).

* cited by examiner

DUAL FUNCTION MICROBICIDES

FIELD OF THE INVENTION

The present invention is directed to cyclohexenyl-substituted thiourea compounds useful in providing contraceptive, e.g. spermicidal, effects. In one particular embodiment, the present invention is directed to novel dual-function cyclohexenyl-substitued thiourea compounds that exhibit both spermicidal activity and potent anti-microbial, particularly anti-viral, activity.

BACKGROUND OF THE INVENTION

Human immunodeficiency virus (HIV), the etiologic agent of acquired immunodeficiency syndrome (AIDS) is the fastest growing cause of death in women of reproductive age [1–31]. Worldwide, heterosexual transmission accounts for 90% of all HIV infections in women [2, 4]. Currently an estimated 14.1 million women worldwide are infected with HIV, representing 44% of all adult infections. Considering that the AIDS pandemic is still in its infancy on a global scale, this evolving demographic situation warrants urgent attention particularly for the adolescent population. Therefore, effective strategies are needed to reduce heterosexual and perinatal HIV transmission. In the absence of an effective prophylactic anti-HIV therapy or vaccine, new emphasis has been placed on the development of intravaginal microbicidal agents capable of reducing the transmission of HIV [5, 6]. In addition, prophylactic contraception is fundamentally important in HIV-infected women for prevention of HIV transmission and pregnancy, especially because 80% of women with AIDS are of childbearing age [7].

At present, all commercially available spermicidal microbicides have detergent ingredients that disrupt cell membranes [8, 9]. The most widely used vaginal spermicide, nonoxynol-9 (N-9), because of its membrane disruptive properties has been shown to damage the cervicovaginal epithelium [10–12], cause an acute inflammatory tissue response [13], alter vaginal microflora [14, 15], and enhance the risk of promoting opportunistic infections in the genitourinary tract [16]. Such opportunistic infections are known to enhance the susceptibility of the ectocervical epithelium and the endocervical mucosa to HIV infection [17–19]. Despite its ability to inactivate HIV in vitro, the reported failure of N-9 to prevent heterosexual vaginal transmission of HIV in clinical settings in addition to its adverse effects on the cervicovaginal epithelium and vaginal microflora has prompted the search for new female-controlled microbicides that are both more effective and safer than N-9 [20–24]. Unlike the detergent-based microbicides that target cell membranes, the intravaginal or intrarectal use of topical formulations of anti-HIV drugs such as non-nucleoside inhibitors (NNIs) might be an effective approach for preventing the sexual transmission of HIV. These inhibitors of viral replication have been proposed by the WHO as candidates for intravaginal microbicides to inhibit HIV replication in mucosal cells [25, 26]. Inasmuch as physiological fertilization is dependent on the ability of ejaculated sperm to swim, bind the zona pellucida, and penetrate the egg, that are primarily dependent on sperm motility, adding spermicidal function to potent anti-HIV drugs could be an effective way to curb heterosexual HIV transmission as well as prevent conception.

Design of potent inhibitors of HIV-1 reverse transcriptase (RT) has been a focal point in translational AIDS research [27–30]. The NNIs are a diverse set of compounds which include tetrahydroimidazobenzodiazepinethione (TIBO) compounds [31], 1-[(2-hydroxyethoxy)methyl]-6-(phenylthio)thymine (HEPT) derivatives [32–35], bis (heteroaryl)piperazine (BHAP) analogs[30], 2'-5'-bis-O-(tertbutyldimethylsilyl)-3'-spiro-5"-(4"-amino-1", 2"-oxathiole-2", 2"-dioxide) pyrimidine (TSAO) [36], dihydroalkoxybenzyloxopyrimidine (DABO) [37, 38], and phenethylthiazolylthiourea (PETT) derivatives [39–42]. These NNIs interfere with the activity of viral RT by binding to a specific allosteric site of HIV-1 RT near the polymerase site and severely limit the conformational flexibility needed for RT function, rendering the viral protein inactive [43–49]. A number of crystal structures of RT complexed with NNIs have been reported, and such structural information has provided the basis for further derivatization of NNI aimed at maximizing binding affinity to RT [44–50].

The success of NNIs for the clinical treatment of AIDS has led us to the computer-aided design and chemical synthesis of mechanism-based anti-retroviral agents that also exhibit spermicidal activity. Recently, we described structure-based design and synthesis of novel NNIs by generating a novel computer model in which a composite binding pocket was constructed from 9 individual crystal structures of RT-NNIs complexes [51, 52]. This computer docking procedure revealed abundant sterically allowed usable space surrounding the pyridyl ring of the thiourea compound, trovirdine. Using this model, we strategically designed novel compounds having functional groups that better fit and interact in the binding pocket space, to obtain more potent anti-HIV agents with higher affinity for the NNI binding pocket of HIV-1 RT that also exhibit spermicidal activity [53]. Continued development of novel agents designed to utilize the spatial and chemical relationships defined in the RT-NNI binding pocket model is needed to obtain alternative potent anti-microbial agents, and preferably, dual-function microbicides exhibiting spermicidal activity.

SUMMARY OF THE INVENTION

The present invention provides novel thiourea compounds that are useful as anti-microbial, e.g., anti-viral, and contraceptive agents, as well as products and methods using these compounds. Examples of such useful products include vaginal foams, creams, lotions or gels, sponges or other vaginal inserts, and condom lubricating compositions. The present invention also is directed to certain thiourea compounds that exhibit contraceptive properties while maintaining activity against microorganisms, such as HIV.

Particularly useful compounds of the invention are cyclohexenyl-substituted thioureas as described more fully below. Specific cyclohexenyl ring-containing thiourea compounds are identified in the Examples below as preferred, potent, dual-function anti-microbial and spermicidal agents. In particular, PHI-346 (N-[2-(5-bromopyridinyl)]-N'-[2-(1-cyclohexenyl)ethyl]-thiourea); and PHI-445 (N-[2-(5-chloropyridinyl)]-N'-[2-cyclohexenyl)ethyl-thiourea), were identified as most preferred dual-function anti-HIV spermicides.

The present invention also provides contraceptive products that utilize the dual function spermicidal thiourea compounds of the invention, preferably substituted cyclohexenyl thiourea compounds, as active agents, and to the production of such contraceptive products.

Methods of the invention include the step of contacting sperm with a spermicidal thiourea compound of the invention, for example by means of a contraceptive product of this invention as discussed above.

DETAILED DESCRIPTION OF THE INVENTION

Compounds of the Invention

Figure 1:
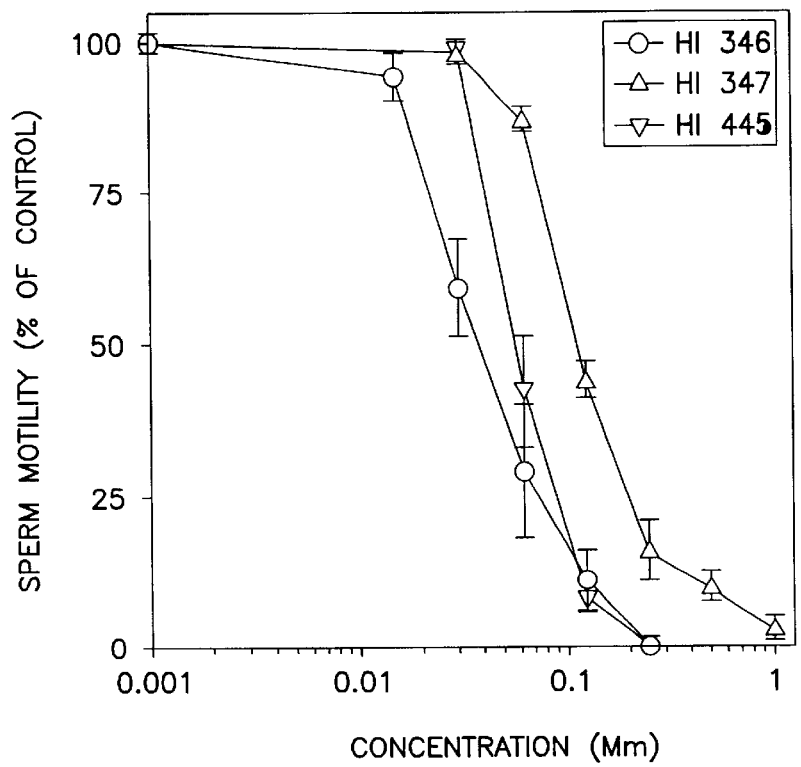
FIG. 1 is a graph showing concentration-dependent inhibition of human sperm motility by cyclohexenyl ring-containing substituted thiourea derivatives. Highly motile fractions of sperm were incubated with increasing concentrations (15.6 µM–1000 µM) of PHI-346, PHI-347, and PHI-445 or 1% DMSO in the assay medium, and the percentage of motile sperm were evaluated by CASA. Each data point represents the mean from three independent experiments.

The compounds of the invention are thiourea compounds useful as potent anti-microbial, particularly anti-HIV, agents as well as spermicidal agents, as demonstrated in the Examples below. The preferred agents exhibit reduced side effects when compared with N-9.

The compounds of the invention have the general structure shown below:

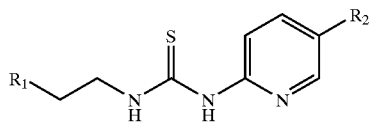

Preferred compounds are those where $R_1$ is cyclohexenyl, preferably 1-cyclohexenyl, and $R_2$ is $CF_3$ or halo, preferably bromo or chloro. Spermicidal compounds of the invention also include those where $R_1$ is pyridyl (e.g., PHI-207) and piperidinyl (e.g., PHI-344).

Cyclohexenyl substituted thiourea derivatives, more particularly 1-cyclohexenyl ring-containing derivatives are preferred dual function agents. 5-bromo (PHI-346) and 5-chloro (PHI-445) functionalized cyclohexenyl ring-substituted thioureas are most preferred.

The heterocyclic and cyclohexenyl-substituted thiourea compounds of the invention, and particularly PHI-346 (N-[2-(5-bromopyridinyl)]-N'-[2-(1-cyclohexenyl)ethyl-thiourea) and PHI-445 (N-[2-(5-chloropyridinyl)]-N'-[2-(1-cyclohexenyl)ethyl-thiourea) are particularly useful as active ingredients of a vaginal contraceptive, for example, in women who are at high risk for acquiring HIV or other microbial infections by heterosexual vaginal transmission.

It will be readily apparent to those skilled in the art that other structures functioning as precursors and derivatives such as salts and esters of the present structures can be developed. The compounds of the invention can be prepared and characterized as described in the Examples below.

Contraceptive Compositions of the Invention

The compounds of the invention, as spermicidal active agents, can be formulated into contraceptive compositions for use. Such compositions are intended particularly for use with mammals, i.e. any class of higher vertebrates that nourish their young with milk secreted from mammary glands, for example humans, rabbits and monkeys. It is expected that the present invention will be used by humans, in most practical applications.

The contraceptive compositions of the present invention contain one or more of the spermicidal thiourea compounds. The total amount of spermicide will typically range from about 0.025 to 0.5 weight percent based on the total weight of the contraceptive composition. The amount of spermicide employed generally will be that amount necessary to achieve the desired spermicidal and anti-viral protective results. The amounts can be varied as needed for specific compositions. Preferably, the amount of the spermicidal thiourea compound employed will be from about 0.05 to 0.5 weight percent, and more preferably from about 0.05 to 0.25 weight percent, based on the total weight of the contraceptive composition.

The contraceptive compositions of the present invention contain not only the spermicidal thiourea compound of the invention, but also pharmaceutically acceptable carriers, diluents or vehicles as needed, i.e., materials for appropriately delivering and/or maintaining the spermicidal thiourea compound to a site for contact with sperm and so as to provide the desired spermicidal and anti-microbial, e.g., anti-viral protective activity.

One advantageous component in the pharmaceutical composition for administration of a spermicide is a polymeric delivery component as described in U.S. Pat. No. 5,595,980, which patent is incorporated herein by reference. It has been found that such polymeric delivery component enhances the effectiveness of a spermicide and reduces vaginal irritation on administration.

In addition to the polymeric component, the balance of the contraceptive compositions, i.e., typically from about 0.1 to 99.8% and, often, about 50 to 99.8 weight percent, may optionally comprise one or more cosmetic ingredients. Such cosmetic ingredients are known to those skilled in the art and are often referred to in the art as diluents, solvents, and adjuvants. Typically cosmetic ingredients include, for example; water, ethyl alcohol, isopropyl alcohol, glycerin, glycerol propylene glycol, sorbitol, and other high molecular weight alcohols. In addition, contraceptive compositions may contain minor amounts, e.g. from about 0.1 to 5% weight based on the weight of the contraceptive compositions, of other additives, such as, for example; stabilizers, surfactants, menthol, eucalyptus oil, other essential oils, fragrances, and the like. Polyoxyethylene 20 sorbitan monolaurate is a preferred stabilizer for use in the compositions. The selection and amounts of cosmetic ingredients, other additives, and blending procedures can be carried out in accordance with techniques well-known in the art.

The spermicidal active ingredients, and contraceptive compositions containing the same, of the present invention may be delivered to the vagina of a mammal by any means known to those skilled in the art. Typical forms for delivery of the compositions include, for example; creams, lotions, gels, foams, intervaginal devices such as sponges and suppositories, and films. In addition, the contraceptive compounds and compositions of the present invention may be used as personal care products, such as, for example, condom lubricants, and the like. Such lubricants may comprise commonly known ingredients such as, for example: humectants; e.g., glycerin, sorbitol, mannitol, glycols and glycol ethers; buffers, e.g., glucono-d-lactone; germicides or bactericides; e.g., chlorhexidine gluconate; preservatives, e.g., methylparaben; viscosifiers; e.g., hydroxyethyl cellulose, etc.; other adjuvants; e.g., colors and fragrances; in addition to the compositions of the present invention. Those skilled in the art will recognize that the physical properties, e.g., viscosity, of such delivery forms may vary widely. For example, the viscosity of a gel form of the composition of the present invention, e.g., 150,000 centipoise, may be substantially higher than the viscosity of lotion form of the composition of the present invention, e.g., 100 centipoise. Further details concerning the materials, ingredients, proportions and procedures of such delivery forms can be selected in accordance with techniques well-known in the art.

The contraceptive compositions of the present invention are preferably administered to the vagina of the mammal in a dosage which is effective to immobilize sperm present in the vagina and/or to inhibit their penetration in cervical mucus. Typical dosages range between about 0.0001 to 0.001 grams of the composition per kilogram of body weight of the mammal.

Intervaginal devices also may be used to aid in the administration of the spermicidal active ingredients or contraceptive compositions containing the same as described in U.S. Pat. No. 5,069,906, the disclosure of which is incorporated herein by reference.

In administering the spermical active ingredients in the form of the above compositions, the compositions also may be formulated to release the spermicide both rapidly and with a prolonged release of the drug. Such a formulation providing both rapid and prolonged release has been described in U.S. Pat. No. 4,707,362, which also is incorporated herein by reference.

EXAMPLES

The invention will be explained further with reference to the following examples, which should not be considered to limit the invention.

Materials And Methods

Reagents and Instrumentation

All chemicals were purchased from Aldrich Chemical Corporation (Milwaukee, Wis.). Anhydrous acetonitrile and N,N-dimethylformamide were transferred to reaction vessels via cannula under nitrogen. All reactions were carried out under nitrogen. Proton ($^1$H), carbon ($^{13}$C), and fluorine ($^{19}$F) nuclear magnetic resonance spectra (NMR) were recorded on a Varian Oxford 300 MHz spectrometer (Varian Associates, Palo Alto, Calif.) using an automated broadband probe. All NMR spectra were recorded in $CDCl_3$. $^{13}$C NMR spectra were recorded using the proton decoupling technique. $^{19}$F NMR spectra were recorded in $CDCl_3$ and a 1% solution of trifluoroacetic acid in water was used as an internal standard in a fused capillary tube. Fourier transform infrared (FT-IR) spectra were recorded using a FT-Nicolet Model Protege 460 instrument (Nicolet Instrument Corp., Madison, Wis.). Mass spectra analyses were performed by using a Model G2025A Hewlett Packard matrix-assisted laser desorption spectrometer (Wilmington, Del.) in the molecular ion detection mode. The matrix used was cyano hydroxy cinnamic acid. Ultraviolet (UV) spectra were recorded from Beckmann Model 3DU 7400 UV-Visible spectrophotometer (Beckmann Instruments, Fullerton, Calif.) using a cell path length of 1 cm. Elemental analysis was performed by MicroLab Inc., (Atlanta, Ga.). Column chromatography was performed using silica gel. The solvents used for elution varied depending on the compound and included one of the following: ethyl acetate, methanol, chloroform, hexane, methylene chloride and ether.

Synthetic Scheme for Substituted Thiourea Derivatives

The names of the 31 thiourea compounds synthesized and tested in this study are listed in Table 1. Thirty (30) novel thiourea compounds were designed as inhibitors of HIV-1 RT, based on a composite binding pocket computer model constructed from nine (9) individual crystal structures of RT-NNI complexes [51, 52]. Modeling studies for rational drug design included the construction of a composite NNI binding pocket for nine RT-NNI crystal structures, the analyses of surface complementarity between NNIs and RT, and application of inhibitory constants ($K_i$ values) combined with a docking procedure involving the novel thiourea compounds [51, 52]. This computational approach allowed the identification of several ligand derivatization sites for the generation of more potent dual-function thiourea compounds. Detailed analysis of trovirdine-binding [51], revealed multiple, specific sites which where larger functional groups could be incorporated in to the NNI. The composite binding pocket, the docked trovirdine molecule showed abundant sterically allowed usable space surrounding the pyridyl ring, the ethyl linker, and near the 5'-bromo position. We hypothesized that addition of strategically designed functional groups would yield more potent anti-HIV agents with contraceptive acitivity (e.g., SIA). A series of thiourea compounds was synthesized, in which one of the nitrogen atoms of the thiourea was attached either to a phenyl, heterocyclic, or alicyclic moiety through a ethyl bridge and the other nitrogen atom was attached to a 5'-bromo or 5'-trifluoromethyl substituted or unsubstituted pyridyl ring.

TABLE 1

Thiourea compounds synthesized and tested

| Compound | Chemical name |
|---|---|
| PHENYL | |
| HI-232 | N-[2-(3,4-dimethoxyphenethyl)]-N'-[2-(5-bromopyridyl)-thiourea |
| HI-236 | N-[2-(2,5-dimethoxyphenethyl)]-N'-[2-(5-bromopyridyl)-thiourea |
| HI-237 | N-[2-(2-methoxyphenethyl)]-N'-[2-(5-bromopyridyl)-thiourea |
| HI-239 | N-[2-(3-methoxyphenethyl)]-N'-[2-(5-bromopyridyl)-thiourea |
| HI-240 | N-[2-(2-fluorophenethyl)]-N'-[2-(5-bromopyridyl)-thiourea |
| HI-241 | N-[2-(3-fluorophenethyl)]-N'-[2-(5-bromopyridyl)-thiourea |
| HI-242 | N-[2-(4-fluorophenethyl)]-N'-[2-(5-bromopyridyl)-thiourea |
| HI-243 | N-[2-(4-bromophenethyl)]-N'-[2-(5-bromopyridyl)-thiourea |
| HI-244 | N-[2-(4-methylphenethyl)]-N'-[2-(5-bromopyridyl)-thiourea |
| HI-253 | N-(2-(2-chlorophenethyl)]-N'-[2-(5-bromopyridyl)-thiourea |
| HI-254 | N-[2-(3-chlorophenethyl)]-N'-[2-(5-bromopyridyl)-thiourea |
| HI-255 | N-[2-(4-chlorophenethyl)]-N'-[2-(5-bromopyridyl)-thiourea |
| HI-256 | N-[2-(4-hydroxyphenethyl)]-N'-[2-(5-bromopyridyl)]thiourea |
| HI-275 | N-[2-(phenethyl)]-N'-[2-(5-bromopyridinyl)-thiourea |
| HI-308 | N-[2-(phenethyl)]-N'-[2-(5-trifluoromethylpyridinyl)]-thiourea |

TABLE 1-continued

Thiourea compounds synthesized and tested

| Compound | Chemical name |
|---|---|
| HI-310 | N-[2-(5-dimethoxyphenethyl)]-N'-[2-(5-trifluoromethylpyridinyl)]-thiourea |
| HI-311 | N-[2-(2-fluorophenethyl]-N'-[2-(5-trifluoromethylpyridinyl)-thiourea |
| HI-345 | N-[2-(3-fluorophenethyl)]-N'-[2-(5-bromopyridyl)-thiourea |
| HETEROCYCLIC | |
| HI-142 | N-[2-(pyridinyl)]-N'-[2-(5-bromopyridinyl)-thiourea (Trovirdine) |
| HI-172 | N-[2-(1-piperidinoethyl)]-N'-[2-(5-bromopyridyl)-thiourea |
| HI-258 | N-[2-(1-piperizinylethyl)]-N'-[2-(5-bromopyridyl)-thiourea |
| HI-230 | N-[2-(1-pyrrolidinylethyl)]-N'-[2-(5-bromopyridyl)-thiourea |
| HI-207 | N-[2-(2-pyridylethyl)]-N'-[2-(pyridyl)-thiourea |
| HI-309 | N-[2-(5-trifluoromethylpyridinyl)]-N'-[2-pyridinyl)]-thiourea |
| HI-344 | N-[2-(5-trifluoromethylpyridinyl)]-N'-[2-(1-piperidinylethyl)-thiourea |
| HI-443 | N-[2-(5-bromopyridinyl)]-N'-[2-(2-thiophenylethyl)-thiourea |
| ALICYCLIC | |
| HI-346 | N-[2-(5-bromopyridinyl)]-N'-[2-(1-cyclohexenyl)ethyl-thiourea |
| HI-347 | N-[2-(5-trifluoromethylpyridinyl)]-N'-[2-(1-cyclohexenyl)ethyl]-thiourea |
| HI-445 | N-[2-(5-chloropyridinyl)]-N'-[2-(1-cyclohexenyl)ethyl-thiourea |
| HI-444 | N-[2-(5-bromopyridinyl)]-N'-[2-(2-myrtanyl)-thiourea |
| HI-541 | N-[2-(2-cyclohexenyl)ethyl-N'-[2-(pyridinyl)]-thiourea |

For the synthesis of novel 5'-substituted pyridyl thiourea compounds, additional substitutions on the phenyl ring included either fluoro, chloro, bromo or methoxy groups at ortho (2,5), meta (3) or para (4) positions on the phenyl ring. The general synthetic scheme followed was detailed in previous reports [51, 52, 56, 57], and is shown below. Trovirdine (N-[2-(pyridyl)]-N'-[2-5-bromopyridinyl)-thiourea), was synthesized according to a literature procedure [42].

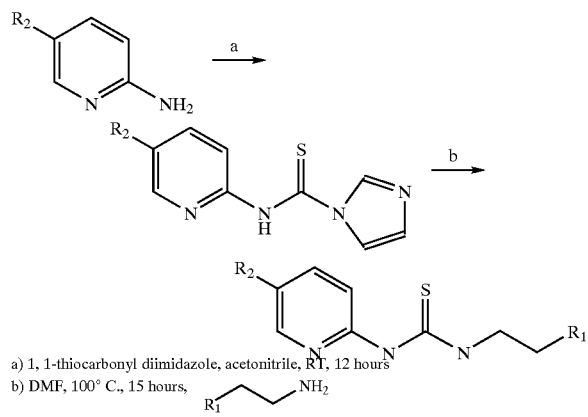

a) 1, 1-thiocarbonyl diimidazole, acetonitrile, RT, 12 hours
b) DMF, 100° C., 15 hours,

Determination of the Partition Coefficients ($P_a$)

Partition of the test compounds between n-octanol and water as a measure of their lipophilicity was determined by taking the UV absorption of each compound in n-octanol, water-saturated n- octanol (1:1), and n-octanol-saturated water (1:1). The UV absorption maxima were determined by selecting a wavelength with the maximum absorption peak in the water-saturated octanol layer and the corresponding peak in the octanol-saturated water. Three absorption spectra were obtained for each compound. The partion coefficient ($P_a$) was calculated as the ratio of the compound concentration present in the lipid phase to the compound concentration present in the aqueous phase.

In Vitro Assays of Anti-HIV Activity

The HTLV$_{IIIB}$ strain of HIV-1 was propagated in CCRF-CEM cells and the virus stocks obtained from cell-free supernatants of infected cells were titered using MT-2 cells [58, 59]. Cell-free supernatants were harvested and frozen in 1 ml aliquots at −70° C. Titration of the stock virus was performed using MT-2 cells and the cytopathic effect of the virus used in this study was typical of HIV-1 on MT-2 cells [58, 59].

For in vitro assays of the anti-HIV-1 activities of phenyl, heterocyclic and alicyclic ring substituted thiourea compounds, normal peripheral blood mononuclear cells (PBMCs) from HIV-1 negative donors were cultured for 72 hours in RPMI 1640 medium (Gibco-BRL, Grand Island, N.Y.) with 20% (v/v) heat-inactivated fetal calf serum, 3% interleukin-2, 2 mM L-glutamine, 25 mM HEPES, 2 g/L NaHCO$_3$, 50 µg/ml gentamicin, and 4 µg/ml phytohemagglutinin prior to exposure to HIV-1 at a multiplicity of infection of 0.1 during a 1 hour adsorption period at 37° C. in a humidified 5% CO$_2$ atmosphere. Stock solutions (10 mM) of thiourea compounds were prepared in dimethylsulfoxide (DMSO). Cells were cultured for 7 days in 96-well microtiter plates (100 µl/well; 2×10$^6$ cells/ml, triplicate wells) in the presence and absence of various concentrations (0.001 µM to 100 µM) of the thioureas. Cells from non-infected controls were handled in the same way except the virus was omitted from the preparation. Aliquots of culture supernatants were removed from the wells on the 7th day after infection for p24 antigen as previously described [59, 60]. The p24 enzyme immunoassay was the unmodified kinetic assay available commercially (Coulter Corporation/Immunotech, Inc., Westbrook, Me.). The assay uses a murine monoclonal antibody (mAb) to the HIV core protein coated onto microwell strips to which the antigen present in the test culture supernatant sample binds [56–58]. The plates were read on a ELISA reader (Molecular Devices, Sunnyvale, Calif.) at 650 nm and p24 levels, expressed as ng/ml, were calculated against known standards supplied by Coulter/Imrunotech, Inc. Percent viral inhibition was calculated by comparing the p24 values for the test substance-treated infected cells with the p24 values for untreated infected cells (i.e., virus controls).

Each of the thirty one thiourea compounds was tested for RT inhibitory activity against purified recombinant HIV-1 RT using the cell-free Quan-T-RT system (Amersham Corp., Arlington Heights, Ill.), which utilizes the scintillation proximity assay principle [61]. The anti-HIV activity was expressed as the IC$_{50}$ value, calculated from the dose-response curves, and defined as the drug concentration that decreases p24 antigen production in HIV-1 infected PBMCs or the HIV-1 rRT activity, by 50%.

Assays of Sperm Immobilizing Activity (SIA)

To evaluate the effect of each of the 31 thiourea compounds on human sperm motility and kinematics, highly motile fractions of sperm were prepared from donor semen (n=8) by discontinuous (90–45%) gradient centrifugation using Enhance Plus medium (Conception Technologies, San Diego, Calif.) and the "swim-up" method [53, 62]. The swim-up method was used after density gradient centrifugation, washing, and resuspension of sperm in BWW-3% BSA. Pooled swim-up fraction was washed once prior to spermicidal assay.

All donor semen specimens were obtained after informed consent and in compliance with the guidelines of the Parker Hughes Institute Institutional Review Board. Pooled motile sperm ($\leq 10 \times 10^6$/ml) prepared from 3–6 donors were suspended in 1 ml of Biggers, Whitten, and Whittingam's medium (BWW) containing 25 mM HEPES (Irvine Scientific, Santa Ana, Calif.), and 0.3% BSA in the presence and absence of serial two-fold dilutions of test substance (500 µM to 15.6 µM) in 0.5% DMSO. The stock solutions of thioureas were prepared in DMSO (100 mM) and diluted in assay medium to yield the desired concentrations (up to 1000 µM). Corresponding volume of DMSO (either 0.5% or 1%) was added to control tubes. After 3 hours of incubation at 37° C., the percentage of motile sperm was evaluated by CASA [53, 62–64]. The percent motilities were compared with sham-treated control suspensions of motile sperm. The SIA of the compounds was expressed as the mean $EC_{50}$ values (the final concentration of the compound in medium that decreases the proportion of motile sperm by 50%) calculated from three independent experiments.

Sperm Kinematic Parameters

For CASA, 5-µl of each sperm suspension was loaded into a 20-µm Microcell slide (Conception Technologies) in a counting chamber at 37° C. At least 5–8 fields per slide were scanned for analysis using a Hamilton Thome Integrated Visual Optical System (IVOS), version 10 instrument (Hamilton Thome Research Inc., Danvers, Mass.). Each field was recorded for 30 seconds. The computer calibrations were set at 30 frames at a frame rate of 30/second. Other settings were as follows: minimum contrast 8; minimum size 6; low-size gate, 1.0; high-size gate, 2.9; low-intensity gate, 0.6; high-intensity gate, 1.4; phase-contrast illumination; low path velocity at 10 µm/s, and threshold straightness at 80%; and magnification factor, 1.95.

The sperm kinematics parameters that were determined included numbers of motile (MOT) and progressively (PRG) motile sperm; curvilinear velocity (VCL; a measure of the total distance traveled by a given sperm during the acquisition divided by the time elapsed); average path velocity (VAP; the spatially averaged path that eliminates the wobble of the sperm head), straight line velocity (VSL; the straight-line distance from beginning to end of track divided by time taken), beat cross frequency (BCF; frequency of sperm head crossing sperm average path), the amplitude of lateral head displacement (ALH; the mean width of sperm head oscillation), and the derivatives, straightness (STR=VSL/VAP×100) and linearity (LIN=VSL/VCL×100; departure of sperm track from a straight line). Data from each individual cell track were recorded and analyzed. At least 200 motile sperm were analyzed for each aliquot sampled.

Assay for Cell Viability

The potential cytotoxicity of two phenyl ring- (PHI-240 and PHI-253), one heterocyclic-ring (PHI-207) and two cyclohexenyl (PHI-346 and 445) ring-containing most potent dual-function thiourea compounds in comparison to N-9, against normal human vaginal, ectocervical, and endocervical epithelial cells (Clonetics Corporation, San Diego, Calif.) was measured using the MTT (3-[4,5-dimethylthiazol-2-yl]-2,5-diphenyl tetrazolium bromide)-based assay [53, 65]. Briefly, exponential growing vaginal, ectocervical, and endocervical epithelial cells were seeded into 96-well plates at a density of $2 \times 10^4$ cells/well and incubated for 24 h at 37° C. prior to drug exposure. On the day of treatment, culture medium was aspirated from the wells and replaced with fresh medium containing serial two-fold drug concentrations ranging from 7.8 µM to 1000 µM. N-9 (IGEPAL CO-630; Rhone Poulenc, Cranbury, N.J.) was diluted in PBS. Triplicate wells were used for each treatment. Culture plates were then incubated for 3 hours before adding 10 µl of MTT solution (5 mg/ml in PBS) to each well. Wells containing only medium and MTT were used as control for each plate. The tetrazolium/formazan reaction was allowed to proceed for 4 hours at 37° C., and then 100 µl of the solubilization buffer (10% sodium dodecyl sulfate in 0.1% HCl) was added to all wells and mixed thoroughly to dissolve the dark blue formazan crystals. After an overnight incubation at 37° C., the OD at 540 nm were measured using a 96-well multiscanner autoreader with the solubilization buffer serving as blank. To translate the $OD_{540}$ values into the number of live cells in each well, the $OD_{540}$ values were compared to those of standard $OD_{540}$-versus-cell number curves generated for each cell line. The percent survival was calculated using the formula: % survival=Live cell number [test]/Live cell number [control]×100. The results were expressed as mean $IC_{50}$ values for three independent experiments. The $IC_{50}$ [MTT] was defined as the concentration required for 50% reduction in cell survival.

Statistical Analysis

Results are presented as the mean or mean ±SD values from independent measurements. Non-linear regression analysis was used to find $IC_{50}$ and $EC_{50}$ values from the concentration-effect curves using the GraphPad PRISM version 2.0 software program (San Diego, Calif.).

Results

Anti-HIV and SIA of Phenyl Thiourea Compounds

Thiourea compounds were assayed for their ability to inhibit HIV-1 replication in normal human PBMCs infected with the HIV-1 strain $HTLV_{IIIB}$ (reported as $IC_{50}$[p24]) as well as for their RT inhibitory activity in cell-free assays using purified recombinant HIV-1 RT (reported as $IC_{50}$ [rRT]). The SIA of thiourea compounds was evaluated by computer-assisted sperm analysis (reported as $EC_{50}$). The lipophilicity of the compounds was measured by their partition coefficients between n-octanol and water (reported as $P_a$).

The effect of ring substitution and functionalization of the pyridyl moiety of the thiourea derivative, trovirdine was tested. Table 2 lists the anti-HIV and SIA profiles of 18 phenyl ring substituted thiourea compounds in which one of the nitrogen atoms of the thiourea is attached to one of 16 different substituted phenyl rings ($R_1$) through an ethyl bridge and the other nitrogen atom is attached to a 5'-bromo or 5'-trifluoromethyl substituted ($R_2$) pyridyl ring. Among the 16 substituted phenyl thiourea derivatives, functionalization of the phenyl ring with 2,5-dimethoxy (PHI-236), 2-fluoro (PHI-240), 3-fluoro (PHI-241), and 2-chloro (PHI-253) was associated with enhanced anti-HIV activity ($IC_{50[p24]}$=<1 nM; $IC_{50[rRT]}$=0.10 µM to 0.70µM) when compared with the unsubstituted phenyl thiourea compound (PHI-275) ($IC_{50[p24]}$=4 nM and $IC_{50[rRT]}$=1.25 µM). In addition, phenyl ring-containing thiourea compounds substituted with 3-methoxy (PHI-239), 4-fluoro (PHI-242), and 4-chloro (PHI-255) functional groups were also potent inhibitors of HIV-1 ($IC_{50[p24]}$=1 nM to 10 nM; $IC_{50[rRT]}$=0.4 µM to 6.4 µM). By comparison, the unsubstituted 5'-trifluoromethyl phenyl thiourea (PHI-308) was inactive and its alkoxy (PHI-310) and halo (PHI-311) substituted derivatives were less potent ($IC_{50[p24]}$ values of 0.08 µM and 0.09 µM and $IC_{50[rRT]}$ values of 2 µM and 0.6 µM, respectively. Thus, the substitution of the phenyl ring with various functional groups had a major impact on the anti-HIV activity of unsubstituted parent compound (PHI-275). Specifically, functionalization of 5-bromo phenyl substituted thiourea derivatives with alkoxy or halo substitutions on the phenyl ring led to superior anti-HIV activity.

Exposure of the highly motile fraction of human sperm to 12 of the 18 substituted phenyl thiourea derivatives listed in Table 2 did not affect sperm motility even at concentrations as high as 500 µM. Notably, halo-functionalized phenyl-substituted thiourea derivatives with 2-fluoro (PHI-240), 2-chloro (PHI-253), and 4-chloro (PHI-255) functional groups showed, in addition to their potent anti-HIV activity ($IC_{50[p24]}$=<1 nM), also spermicidal activity with $EC_{50}$ values of 147 µM, 70 µM, and 160 µM, respectively (Table 2). Thus, halo substitution of the phenyl ring was essential for the SIA of phenyl thiourea compounds.

TABLE 2

Effect of 18 phenyl ring substituted thiourea compounds on p24 antigen production in HIV-infected PBMC, enzymatic activity of HIV-1 rRT, and human sperm motility.

| Compound | $R_1$ | $R_2$ | $IC_{50}$ [p24]$^a$ (µM) | $IC_{50}$ [rRT]$^b$ (µM) | $EC_{50}$ [SIA]$^c$ (µM) | $P_a^d$ |
|---|---|---|---|---|---|---|
| HI 232 | 3,4-dimethoxy | Br | ND$^e$ | >100 | >500 | 22.7 |
| HI 236 | 2,5-dimethoxy | Br | <0.001 | 0.10 | >500 | 1.78 |
| HI 237 | 2-methoxy | Br | 0.01 | 1.0 | >500 | 3.79 |
| HI 239 | 3-methoxy | Br | 0.003 | 0.40 | >500 | 1.07 |
| HI 240 | 2-fluoro | Br | <0.001 | 0.60 | 147 ± 18 | 1.20 |
| HI 241 | 3-fluoro | Br | <0.001 | 0.70 | >500 | ND |
| HI 242 | 4-fluoro | Br | 0.009 | 6.40 | >500 | 10.7 |
| HI 243 | 4-bromo | Br | 0.07 | 0.90 | >500 | 4.16 |
| HI 244 | 4-methyl | Br | 0.03 | 0.70 | >500 | 1.49 |
| HI 256 | 4-hydroxy | Br | 3.06 | 87.7 | 233 ± 68 | 2.93 |
| HI 253 | 2-chloro | Br | <0.001 | 0.70 | 70 ± 8 | 1.04 |
| HI 254 | 3-chloro | Br | 0.01 | 3.10 | >500 | 6.20 |
| HI 255 | 4-chloro | Br | 0.001 | 2.50 | 160 ± 16 | 2.23 |
| HI 275 | H | Br | 0.004 | 1.25 | 361 ± 31 | 3.50 |
| HI 308 | H | $CF_3$ | ND | >100 | >500 | ND |
| HI 310 | 2,5-dimethoxy | $CF_3$ | 0.08 | 2.00 | 276 ± 22 | 1.00 |
| HI 311 | 2-fluoro | $CF_3$ | 0.09 | 0.60 | >500 | 5.13 |
| HI 345 | 3-fluoro | $CF_3$ | ND | 0.70 | >500 | 1.51 |

$^a IC_{50}$ [p24], Drug concentration inhibiting HIV-p24 antigen production by 50%.
$^b IC_{50}$ [rRT], Drug concentration inhibiting HIV-rRT activity by 50%.
$^c EC_{50}$ [SIA], Drug concentration inhibiting sperm motility by 50%.
$^d P_a$, Partition coefficient.
$^e$ND, not determined.

The SIA of these dual-function thiourea derivatives was not related to their partition coefficient values (Table 2). The spermicidal compounds PHI-240, PHI-253, PHI-255, and PHI-275 had low $P_a$ values (range 1.04 to 3.50). The lack of a correlation between the $P_a$ values and the biological activity of phenyl substituted thiourea derivatives demonstrates that these properties are not dependent on the lipophilicity of the compounds.

Anti-HIV and SIA of Heterocyclic Thiourea Compounds

Next, we synthesized a series of thiourea derivatives in which one of the nitrogen atoms of the thiourea is attached to one of 5 different heterocyclic substitutents ($R_1$) through an ethyl bridge and the other nitrogen atom is attached to a 5-bromo or 5-trifluoromethyl substituted pyridyl ring. Table 3 lists the anti-HIV and SIA profiles 5 heterocyclic ring-substituted thiourea derivatives with and without 5-bromo or 5-trifluoromethyl functionalization ($R_2$) on the pyridine ring. When compared with trovirdine (listed as PHI-142), both the piperdinyl (PHI-172) and piperazinyl (PHI-258)-containing thiourea derivatives were more potent in inhibiting the replication of HIV-1 strain $HTLV_{IIIB}$ in human PBMC with $IC_{50}$ values of <1 nM and 2 nM, respectively, but they lacked SIA ($EC_{50}$ values=>500 µM). Among the 8 heterocyclic thiourea derivatives tested, the 5-bromo functionalized thioureas (PHI-172, PHI-258 and trovirdine) were more potent than trifluoromethyl substituted (PHI-309) or unsubstituted thioureas (PHI-207). Unlike trovirdine, which lacked SIA, the unsubstituted pyridyl thiourea (PHI-207) exhibited anti-HIV activity ($IC_{50[p24]}$=0.27 µM) as well as SIA ($EC_{50}$=279 µM). In addition, the more lipophilic piperidinyl derivative of trifluoromethyl functionalized thiourea (PHI-344) exhibited SIA ($EC_{50}$=131 µM), but it lacked anti-HIV activity ($IC_{50[rRT]}$=>100 µM) (Table 3).

TABLE 3

Effect of 8 heterocylic ring substituted thiourea compounds on p24 antigen production in HIV-infected PBMC, enzymatic activity of HIV-1 rRT, and human sperm motility.

| Compound | $R_1$ | $R_2$ | $IC_{50}$ [p24]$^a$ (µM) | $IC_{50}$ [rRT]$^b$ (µM) | $EC_{50}$ [SIA]$^c$ (µM) | $P_a^d$ |
|---|---|---|---|---|---|---|
| Trovirdine | (Pyridyl) | Br | 0.007 | 0.8 | >500 | 5.3 |
| HI 172 | (Piperidinyl) | Br | <0.001 | 5.8 | >500 | 8.91 |

TABLE 3-continued

Effect of 8 heterocylic ring substituted thiourea compounds on p24 antigen production in HIV-infected PBMC, enzymatic activity of HIV-1 rRT, and human sperm motility.

| Compound | $R_1$ | $R_2$ | $R_2$ | $IC_{50}$ [p24][a] ($\mu$M) | $IC_{50}$ [rRT][b] ($\mu$M) | $EC_{50}$ [SIA][c] ($\mu$M) | $P_a$[d] |
|---|---|---|---|---|---|---|---|
| HI 258 | (Piperazinyl) | | Br | 0.002 | >100 | >500 | 5.92 |
| HI 230 | (Pyrrolidinyl) | | Br | 1.0 | >100 | >500 | 7.91 |
| HI 207 | (Pyridyl) | | H | 0.27 | 0.39 | 279 ± 43 | 2.32 |
| HI 309 | (Pyridyl) | | $CF_3$ | $ND^e$ | 13.9 | >500 | 3.81 |
| HI 344 | (Piperidinyl) | | $CF_3$ | ND | >100 | 131 ± 5 | 10.27 |
| HI 443 | (Thiophene) | | Br | 0.03 | 5.3 | >500 | ND |

[a]$IC_{50}$ [p24], Drug concentration inhibiting HIV-p24 antigen production by 50%.
[b]$IC_{50}$ [rRT], Drug concentration inhibiting HIV-rRT activity by 50%.
[c]$EC_{50}$ [SIA], Drug concentration inhibiting sperm motility by 50%.
[d]$P_a$, Partition coefficient.
[e]ND, not determined.

Anti-HIV and SIA of Alicyclic Thiourea Compounds

In addition to the compounds described above bearing phenyl and heterocyclic rings with and without 5'-functionalization, we also examined the effect of alicyclic ring-containing thiourea compounds. Table 4 lists the anti-HIV and SIA profiles of 5 alicyclic-substituted thiourea derivatives. Replacement of the pyridyl ring of trovirdine with a cis-myrtanyl (PHI-444) resulted in loss of anti-HIV activity, whereas replacement with a cyclohexenyl ring did not. The unsubstituted cylohexenyl ring-containing inhibitor (PHI-541) lacked SIA ($EC_{50}$=>500 $\mu$M). However, functionalization at the 5'-position of the pyridyl ring of cyclohexenyl ring-containing thioureas with a bromine or a chlorine atom led to a significant increase in anti-HIV activity as well as gain of spermicidal function.

TABLE 4

Effect of 4 alicyclic ring substituted PETT derivatives on p24 antigen production in HIV-infected PBMC, enzymatic activity of HIV-1 rRT, and human sperm motility.

| Compound | $R_1$ | $R_2$ | $IC_{50}$ [p24][a] ($\mu$M) | $IC_{50}$ [rRT][b] ($\mu$M) | $EC_{50}$ [SIA][c] ($\mu$M) | $P_a$[d] |
|---|---|---|---|---|---|---|
| Trovirdine | Pyridyl | Br | 0.007 | 0.8 | >500 | 5.3 |
| HI 444 | Cis-Myrtanyl | Br | $ND^e$ | >100 | >500 | 2.1 |
| HI-541 | Cyclohexenyl | H | 0.010 | 5.3 | >500 | ND |

TABLE 4-continued

Effect of 4 alicyclic ring substituted PETT derivatives
on p24 antigen production in HIV-infected PBMC,
enzymatic activity of HIV-1 rRT, and human sperm motility.

| Compound | $R_1$ | $R_2$ | $IC_{50}$ [p24][a] ($\mu$M) | $IC_{50}$ [rRT][b] ($\mu$M) | $EC_{50}$ [SIA][c] ($\mu$M) | $P_a^d$ |
|---|---|---|---|---|---|---|
| HI 346 | Cyclohexenyl | Br  | 0.003 | 0.6 | 42 ± 9  | 8.6 |
| HI 445 | Cyclohexenyl | Cl  | 0.003 | 0.5 | 57 ± 5  | 6.3 |
| HI 347 | Cyclohexenyl | CF$_3$ | 0.079 | 4.0 | 131 ± 4 | 11.5 |

Cyclohexenyl ring substituted thiourea derivatives with either 5-bromo (PHI-346) or 5-chloro (PHI-445) functionalization were the most potent dual-function agents with $IC_{50[p24]}$ values of 3 nM and $EC_{50}$ values of 42 $\mu$M and 57 $\mu$M, respectively. Both of these compounds also inhibited HIV-1 RT activity with $IC_{50}$ values of 0.6 $\mu$M and 0.5 $\mu$M, respectively. By comparison, the anti-HIV activity of the trifluoromethyl substituted cyclohexenyl thiourea derivative (PHI-347) was 26-fold less active and its SIA two to three-fold less active than those of halo functionalized thiourea derivatives. Thus, the potency order for SIA of cyclohexenyl substituted thiourea derivatives was bromo>chloro>trifluoromethyl. Spermicidal cyclohexenyl ring-containing thiourea derivatives had higher $P_a$ values (6.3–11.5) than the inactive cis-myrtanyl substituted (2.1) thiourea derivative (PHI-444), suggesting that the biological activity of cyclohexenyl thiourea derivatives may in part be related to their increased lipophilicity.

Figures 2A, 2B, 2C:
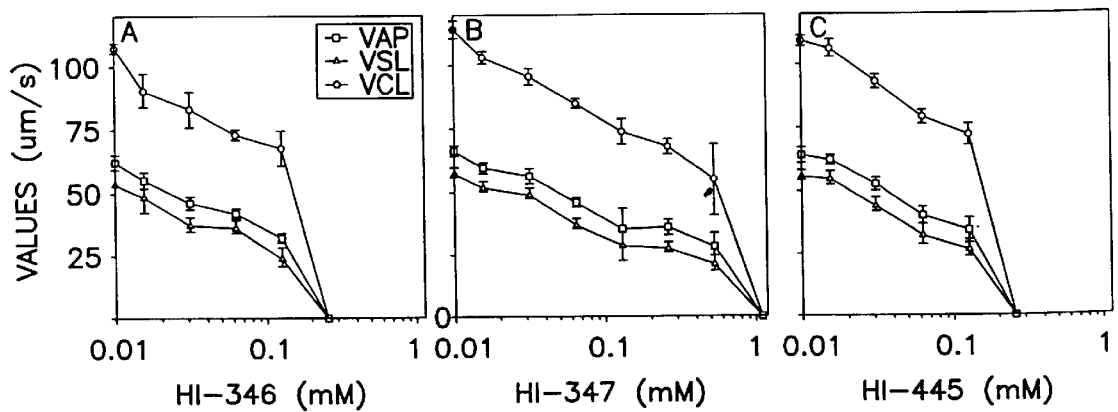
FIGS. 2A–2C are graphs showing the concentration-dependent effect of cyclohexenyl ring containing substituted thiourea derivatives on human sperm motion kinematics. Highly motile fraction of sperm were incubated with increasing concentrations of substituted cyclohexenyl thioureas or 1% DMSO in the assay medium, and their effects on, average path velocity (VAP), straight line velocity (VSL) and curvilinear velocity were evaluated by CASA. Results are expressed as the mean ±SD for 3 separate experiments. PHI-346 (A); PHI-347 (B); and PHI-445(C).

All three cyclohexenyl ring-containing thioureas with additional substitutions on the 5'-position of the pyridyl ring induced a concentration-dependent SIA (FIG. 1). The effective 100% inhibitory concentration ($EC_{100}$) was obtained at 0.25 mM for compounds PHI-346 and PHI-347, and at 1 mM for PHI-445. The concentration-dependent sperm motility loss induced by cyclohexenyl-substituted thiourea derivatives was also associated with significant changes in the movement characteristics of the surviving sperm particularly with respect to track speed (VCL), path velocity (VAP), and straight line velocity (VSL). The representative sperm kinematic parameters of cyclohexenyl-substituted thiourea-treated sperm versus concentration is shown in FIGS. 2A–2C.

As shown in the Figures, the decreases in VSL and VCL or VSL and VAP were similar in magnitude. Therefore, values for linearity (LIN) of the sperm tracks and the straightness (STR) of the swimming pattern remained relatively constant. Also, the beat cross frequency (BCF), and the amplitude of lateral sperm-head displacement (ALH) were relatively stable as the proportion of motile sperm declined during the linear phase of motility loss. The sperm motion parameters of control sperm showed no significant changes (data not shown).

Selective Spermicidal Activity of Dual-Function Thiourea Compounds

In order to determine whether the observed SIA was due to nonspecific membrane damaging effect of dual-function thiourea derivatives, the potential cytotoxicity of five most potent dual-function thiourea derivatives versus N-9 was tested against confluent monolayers of normal human vaginal, ectocervical, and endocervical epithelial cells using the MTT assay. Cells were exposed to these compounds at concentrations ranging from 7.8 $\mu$M to 1000 $\mu$M for 3 hours. The concentration-dependent cell survival curves for dual-function thiourea derivatives versus N-9 for these cells measured by the MTT assay were compared with the SIA measured by CASA (Table 5). In MTT assays, N-9 exhibited significant cytotoxicity to normal human vaginal, ectocervical and endocervical epithelial cells at spermicidal concentrations ($EC_{50}$=81 $\mu$M) with mean $IC_{50[MTT]}$ values of 64 $\mu$M (SI=0.7), 58 $\mu$M (SI=0.7), and 32 $\mu$M (SI=0.3), respectively. By comparison, the $IC_{50[MTT]}$ values for the most potent spermicidal dual-function thiourea derivatives against normal human vaginal, ectocervical, and endocervical epithelial cells were well above their spermicidal $EC_{50}$ values (SI range=>6.8 to >23.8). Thus, unlike N-9 which was spermicidal only at cytotoxic concentrations, dual-function spermicidal thiourea derivatives showed high selectivity indices against these cells. Thus, spermicidal dual-function thiourea derivatives were significantly less active against reproductive tract epithelial cells.

TABLE 5

Effect of spermicidal thiourea compounds on the cell viability of normal human vaginal, ectocervical and endocervical epithelial cells as quantitated by MTT assay.

| Compound | HIV $IC_{50[p24]}$ ($\mu$M)[b] | Sperm $EC_{50[SIA]}$ ($\mu$M)[c] | Vaginal epithelial cells[a] $IC_{50[MTT]}$ ($\mu$M)[d] | SI[e] | Ectocervical epithelial cells[a] $IC_{50[MTT]}$ ($\mu$M) | SI | Endocervical epithelial cells[a] $IC_{50[MTT]}$ ($\mu$M) | SI |
|---|---|---|---|---|---|---|---|---|
| HI-207 | 0.27 | 279 | >1000 | >3.5 | >1000 | >3.5 | >1000 | >3.5 |
| HI-240 | <0.001 | 147 | >1000 | >6.8 | >1000 | >6.8 | >1000 | >6.8 |
| HI-253 | <0.001 | 70 | >1000 | >14.2 | >1000 | >14.2 | >1000 | >14.2 |
| HI-346 | 0.003 | 42 | >1000 | >23.8 | 765 ± 400 | 18.2 | 580 ± 48 | 13.8 |
| HI-445 | 0.003 | 57 | 578 ± 25 | 10.1 | 692 ± 139 | 12.1 | 185 ± 21 | 3.2 |
| N-9 | NA[f] | 81 | 64 ± 3 | 0.7 | 58 ± 1 | 0.7 | 32 ± 1 | 0.4 |

[a]Confluent monolayer cultures of normal human vaginal, ectocervical, and endocervical epithelial cells in 96-well plates were incubated in the absence and presence of increasing two-fold concentrations (7.8 $\mu$M to 1000 $\mu$M) of 5 potent dual-function PETT derivatives for 3 h at 37° C. Cell viability was measured by the MTT assay.
[b]$IC_{50[p24]}$=Drug concentration inhibiting HIV-p24 antigen production by 50%.
[c]$EC_{50}$=Drug concentration inhibiting sperm motility by 50%.
[d]$IC_{50[MTT]}$=Drug concentration inhibiting cell growth by 50%; data are mean ±SD of three experiments.
[e]SI=Selectivity Index is equal to the ratio of $IC_{50}$ to $EC_{50}$.
[f]NA=Not applicable.

While a detailed description of the present invention has been provided above, the invention is not limited thereto. This description contains numerous literature and patent citations, each of which is hereby incorporated by reference for all purposes, as if fully set forth. The invention described herein may be modified to include alternative embodiments, as will be apparent to those skilled in the art. All such alternatives should be considered within the spirit and scope of the invention, as claimed below.

REFERENCES

1. Celum C L, Watts D H. HIV and women. In: Spach D L, Hooton R M (eds.) The HIV manual. New York: Oxford University Press; 1996: 120–127.
2. Quinn T C. Global burden of the HIV pandemic. Lancet 1996; 348:99–106.
3. Osborn J E. Women and HIV/AIDS: the silent epidemic. Sex Info Educ Council US Rep 1991; 19:1–4.
4. Mann J, Tarantola D. The global AIDS pandemic. In: Velji AM (ed.), Infectious Disease Clinics of North America. Philadelphia: Saunders; 1995: 275–285.
5. Potts M. The urgent need for a vaginal microbicide in the prevention of HIV transmission. [Editorial] Am J Public Health 1994; 84:890–891.
6. Uckun F M, D'Cruz O J. Prophylactic contraceptives for HIV/AIDS. Hum Reprod Update 1999; 5:506–514.
7. CDCP Update: US HIV and AIDS cases reported through December 1996. HIV/AIDS Surveillance Report 1997; 8:1–33.
8. OTC Panel. Vaginal contraceptive drug products for over-the counter human use. Federal Register 1980; 45:82014–82049.
9. Chantler E. Vaginal spermicides: some current concerns. British Family Planning 1992; 17:118–119.
10. Niruthisard S R, Roddy E, Chutivongse S. The effects of frequent nonoxynol-9 use on the vaginal and cervical mucosa. Sex Transm Dis 1991; 18:176–179.
11. Roddy R E, Cordero M, Cordero C, Fortney J A. A dosing of nonoxynol-9 and genital irritation. Int J STD & HIV 1993; 4:165–170.
12. Weir S S, Roddy R E, Zekeng L, Feldblum P J. Nonoxynol-9 use, genital ulcers, and HIV infection in a cohort of sex workers. Genitourin Med 1995; 71:78–81.
13. Tryphonas L, Buttar H S. Morphological evidence for vaginal toxicity of Delfan contraceptive cream in the rat. Toxicol Lett 1984; 20:289–295.
14. Rosenstein I J, Stafford M K, Kitchen V S, Ward H, Weber J N, Taylor-Robinson D. Effect of normal vaginal flora of three intravaginal microbicidal agents potentially active against human immunodeficiency virus type 1. J Infect Dis 1998; 177:1386–1390.
15. Hooten T M, Hillier S, Johnson C, Roberts P L, Stamm W E. *Eschericia coli* bacteriuria and contraceptive method. JAMA 1991; 265:64–69.
16. Stafford M K, Ward H, Flanagan A, Rosenstein I J, Taylor-Robinson D, Smith J R, Weber J, Kitchen V S. A safety of nonoxynol-9 as a vaginal microbicide: evidence of adverse effects. J Acquir Immune Defic Syndr Hum Retrovirol 1998; 17:327–331.
17. McGroarty J A, Chong S, Reid G, Bruce A W. Influence of the spermicidal compound nonoxynol-9 on the growth and adhesion of urogenital bacterial in vitro. Curr Microbiol 1990; 21:219–223.
18. Mati J K, Hunter D F, Maggwa B N, Tukei P M. Contraceptive use and the risk of HIV infection in Nairobi, Kenya. Int J Obstet Gynecol 1995; 48:61–67.
19. Wright T C Jr, Ellerbrock T V, Chiasson M A, Van Devanter N, Sun X W. Cervical intraepithelial neoplasia in women infected with human immunodeficiency virus: prevalence, risk factors, and validity of Papanicolaou smears: New York Cervical Disease Study. Obstet Gynecol 1994; 84:591–597.
20. Kreiss J, Ngugi E, Holmes K, Ndinya A J, Waiyaki P, Roberts P L, Ruminjo I, Ajabi R, Kimata J, Fleming T R, Anzala A, Holton D, Plummer F. Efficacy of nonoxynol-9 contraceptive sponge use in preventing heterosexual transmission of HIV in Nairobi prostitutes. JAMA 1992; 268:477–482.
21. Roddy R E, Zeking L, Ryan K A, Tamoufe U, Weir S S, Wong E L. A controlled trial of nonoxynol-9 film to reduce male-to-female transmission of sexually transmitted diseases. N Engl J Med 1998; 339:504–510.
22. Hira S K, Feldblum P J, Kamanga J, Mukelabai G, Weir S S, Thomas J C. Condom and nonoxynol-9 use and the incidence of HIV infection in serodiscordant couples in Zambia. Int J STD AIDS 1997; 8:243–250.
23. Cook R L, Rosenberg M J. Do spermicides containing nonoxynol-9 prevent sexually transmitted infections? Sex Transm Dis 1998; 25:144–150.
24. Rekart M L. The toxicity and local effects of the spermicide nonoxynol-9. J Acquir Immune Defic Syndr 1992; 5:425–427.
25. Lange J M A, Karam M, Plot P. Boost for vaginal microbicides against HIV. Lancet 1993; 341:1356–1359.
26. Cookson C. WHO to concentrate HIV strategy on vaginal microbicide. Br Med J 1993; 307:1375–1376.
27. Mitsuya H, Yarchoan R, Broder S. Molecular targets for AIDS therapy. Science 1990; 249:1533–1544.
28. Greene W C. The molecular biology of human immunodeficiency virus type 1 infections. N Engl J Med 1991; 324:308–317.
29. De Clercq E. Inhibitors targeted at the reverse transcriptase. J Acquired Immune Defic Syndr Res Human Retrovirus 1992; 8:119–134.
30. Hsiou Y, Das K, Ding J, Clark A D Jr, Kleim J P, Rosner M, Winkler I, Riess G, Hughes S H, Arnold E. Structure of tyr188Leu mutant and wild-type HIV-1 reverse transcriptase complexed with the non-nucleoside inhibitor HBY 097: inhibitor flexibility is a useful design feature for reducing drug resistance. J Mol Biol 1998; 284:313–323.
31. Pauwels R, Andries K, Desmyter J, Schols D, Kukla M J, Breslin H J, Raeymaeckers A, Van Gelder J, Woestenborghs R, Heykants J, Schellekens K, Janssen M A C, De Clercq E, Janssen P A. Potent and selective inhibition of HIV-1 replication in vitro by a novel series of TIBO derivatives. Nature 1990; 343:470–474.
32. Tanaka H, Baba M, Hayakawa H, Sakamaki T, Miyasaka T, Ubasawa M, Takashima H, Sekiya K, Nitta I, Shigeta S, Walker R T, Balzarini J, De Clercq E. A new class of HIV-1 -specific 6-substituted acyclouridine derivatives: synthesis and anti-HIV-1 activity of 5- or 6-substituted analogues of 1-[(2-hydroxyethoxy)methyl]-6-(phenylthio)thymine (HEPT). J Med Chem 1991; 34:349–357.
33. Baba M, Shigeta S, Tanaka H, Miyasaka T, Ubasawa M, Umezu K, Walker R T, Pauwels R, De Clercq E. Highly potent and selective inhibition of HIV-1 replication by 6-phenylthiouracil derivatives. Antiviral Res 1992; 17:245–264.
34. Danel K, Larsen E, Pedersen E B, Vestergaard B F, Nielsen C. Synthesis and potent anti-HIV-1 activity of novel 6-benzyluracil analogues of 1-[(2-hydroxyethoxy) methyl]-6-(phenylthio)thymine. J Med Chem 1996; 39:2427–2431.

35. Pontikis R, Benhida R, Aubertin A M, Grierson, D S, Monneret C. Synthesis and anti-HIV activity of novel N-1 side chain-modified analogs of 1-[(2-hydroxyethoxy) methyl]-6-(phenylthio)thymine (HEPT). J Med Chem 1997; 40:1845–1854.

36. Romero D L, Morge, R A, Genin M J, Biles C, Busso M, Resnick L, Althaus I W, Reusser F, Thomas R C, Tarpley W G. Bis(heteroaryl)piperazine (BHAP) reverse transcriptase inhibitors: structure-activity relationships of novel substituted indole analogues and the identification of 1-[(5-methanesulfonamido-lH-indol-2-yl)-carbonyl]-4-[3-[(1-methylethyl)amino]-pyridinyl]piperazine monomethanesulfonate (U-90152S), a second-generation clinical candidate. J Med Chem 1993; 36:1505–1508.

37. Balzarini J, Perez M J, San Felix A, Schols D, Perno C F, Vandamme A M, Camarasa M J, De Clercq E. 2', 5'-Bis-O-(tert-butyldimethylsilyl)-3'-spiro-5"-(4"-amino-1", 2"- oxathiole-2", 2'-dioxide)pyrimidine (TSAO) nucleoside analogues: highly selective inhibitors of human immunodeficiency virus type 1 that are targeted at the viral reverse transcriptase. Proc Natl Acad Sci USA 1992; 89:4392–4396.

38. Mai A, Artica M, Sbardella G, Quartarone S, Massa S, Loi A G, Montis A D, Scintu F, Putzolu M, La Colla P. Dihydro(alkylthio)(naphthylmethyl)oxopyrimidines: Novel non-nucleoside reverse transcriptase inhibitors of the S-DABO series. J Med Chem 1997; 40:1447–1454.

39. Danel K, Pedersen E B, Nielsen C. Synthesis and anti-HIV-1 activity of novel 2,3-dihydro-7H-thiazolo[3, 2-a]pyrimidin-7-ones. J Med Chem 1998; 41:191–198.

40. Ahgren C, Backro K, Bell F W, Cantrell A S, Clemens M, Colacino J M, Deeter J B, Engelhardt J A, Jaskunas J M, Johansson N G, Jordan C L, Kasher J S, Kinnick M D, Lind P, Lopez C, Morin J M J, Muesing M A, Noreen R, Oberg B, Paget C J, Palkowitz J A, Parrish C A, Pranc P, Rippy M K, Rydergard C, Sahlberg C, Swanson S, Temansky R J, Unge T, Vasileff R T, Vrang L, West S J, Zhang H, Zhou X X. The PETT series, a new class of potent nonnucleoside inhibitors of human immunodeficiency virus type 1 reverse transcriptase. Antimicrob Agents Chemother 1995; 39:1329–1335.

41. Bell F W, Cantrell A S, Hogberg M, Jaskunas S R, Johansson N G, Jordan C L, Kinnick M D, Lind P, Morin J M, Jr, Noreen R, Oberg B, Palkowitz J A, Parrish C A, Pramo P, Sahlberg C, Temansky R T, Vasileff R T, Vrang L, West S J, Zhang H, Zhou X X. Phenethylthiazolethiourea (PETT) compounds, a new class of HIV-1 reverse transcriptase inhibitors. 1. Synthesis and basic structure-activity relationship studies of PETT analogs. J Med Chem 1995; 38:4929–4936.

42. Cantrell A S, Engelhardt P, Hogberg M, Jaskunas S R, Johansson N G, Jordan C L, Kangasmetsa J, Kinnick M D, Lind P, Morin J M, Jr, Muesing M A, Noreen R, Oberg B, Pranc P, Sahlberg C, Temansky R J, Vasileff R T, Vrang L, West S J, Zhang H. Phenethylthiazolylthiourea (PETT) compounds as a new class of HIV-1 reverse transcriptase inhibitors. 2. Synthesis and further structure-activity relationship studies of PETT analogs. J Med Chem 1996; 39:4261–4274.

43. Heinisch G, Matuszczak B, Pachler S, Rakowitz D. The inhibitory activity of diazinyl-substituted thiourea derivatives on human immunodeficiency virus type 1 reverse transcriptase. Antivir Chem Chemother 1997; 8:443–446.

44. Hogberg M, Sahlberg C, Engelhardt P, Noreen R, Kangasmetsa J, Johansson N G, Oberg B, Vrang L, Sahlberg B L, Unger T, Logren S, Fridborg K, Backbro K. Urea-PETT compounds as a new class of HIV-reverse transcriptase inhibitors. 3. Synthesis and further structure-activity relationship studies of PETT analogues. J Med Chem 1999; 42:4150–4160.

45. Ding J, Das K, Moereels H, Koymans L, Andries K, Jansen P A, Hughes S H, Arnold E. Structure of HIV-1 RT/TIBO R 86163 complex reveals similarity in the binding of diverse nonnucleoside inhibitors. Nat Struct Biol 1995; 2:407–415.

46. Ding J, Das K, Tantillo C, Zhang W, Clark Jr, A D, Jessen S, Lu X, Hsiou Y, Jacobo-Molina A, Andries K, Pauwels R, Moereels H, Koymans L, Janssen P A J, Smith R H J, Kroeger-Koepke R, Michejda C J, Hughes S H, Arnold E. Structure of HIV-1 reverse transcriptase in a complex with the non-nucleoside inhibitor alpha-APA R 95845 at 2.8 A resolution. Structure 1995; 3:365–379.

47. Kohlstaedt L A, Wang J, Friedman J M, Rice P A, Steitz T A. Crystal structure at 3.5 A resolution of HIV-1 reverse transcriptase complexed with an inhibitor. Science 1992; 256:1783–1790.

48. Ren J, Esnouf R, Garman E, Somers D, Ross C, Kirby I, Keeling J, Darby G, Jones Y, Stuart D, Stammers D. High resolution structures of HIV-1 RT from four RT-inhibitor complexes. Nat Struct Biol 1995; 2:293–302.

49. Ren J, Esnouf R, Hopkins A, Ross C, Jones Y, Stammers D, Stuart D. The structure of HIV-1 reverse transcriptase complexed with 9-chloro-TIBO: lessons for inhibitor design. Structure 1995; 3:915–926.

50. Smerdon S J, Jager J, Wang J, Kohlstaedt L A, Chirino A J, Friedman J M, Rice P A, Steitz T A. Structure of the binding site for nonnucleoside inhibitors of the reverse transcriptase of human immunodeficiency virus type 1. Proc Natl Acad Sci USA 1994; 91:3911–3915.

51. Vig R, Mao C, Venkatachalam T K, Tuel-Ahlgren L, Sudbeck E, Uckun F M. Rational design and synthesis of phenethyl-5-bromopyridyl thiourea derivatives as potent non-nucleoside inhibitors of HIV reverse transcriptase. Bioorg Med Chem 1998; 6:1789–1797.

52. Mao C, Sudbeck E, Venkatachalam T K, Uckun F M. Structure-based drug design of non-nucleoside inhibitors for wild type and drug resistant HIV reverse transcriptase. Biochem Pharmacol 2000 (in press).

53. D'Cruz O J, Uckun F M. Novel derivatives of phenethyl-5-bromopyridylthiourea and dihydroalkoxybenzyloxopyrimidine are dual-function spermicides with potent antihuman immunodeficiency virus activity. Biol Reprod 1999; 60:1419–1428.

54. Quayle A J, Xu C, Mayer K H, Anderson D J. T lymphocytes and macrophages, but not motile spermatozoa, are a significant source of human immunodeficiency virus in semen. J Infect Dis 1997; 176:960–968.

55. Baccetti B, Benedetto A, Burrini A G, Collodel G, Ceccarini C, Crisa E, DiCaro A, Garbuglia A R, Massacesi A, Piomboni P, Solazzo D. HIV-1 particles in spermatozoa of patients with AIDS and their transfer into the oocytes. J Cell Biol 1994; 127:903–914.

56. Mao C, Vig R, Venkatachalam T K, Sudbeck E A, Uckun F M. Structure-based design of N-[2-(1-piperidinylethyl)]-N'-[2-(5-bromopyridyl)-thiourea and N-[2-(1-piperzainylethyl)]-N'-[2-(5-bromopyridyl)]-thiourea as potent non-nucleoside inhibitors of HIV-1 reverse transcriptase. Bioorg Med Chem Lett 1998; 8:2213–1118.

57. Uckun F M, Mao C, Pendergrass S, Maher D, Zhu D, Tuel-Ahlgren L, Venkatachalam T K. and N-[2-(1-cyclohexenyl)ethyl)]-N'-[2-(5-bromopyridyl)]-thiourea and N-[2-(1-cyclohexenyl)ethyl)]-N'-[2-(5- chloropyridyl)]-thiourea as potent inhibitors of multidrug-resistant human immunodeficiency virus-1. Bioorg Med Chem Lett 1999; 9:2721–2726.
58. Uckun F M, Chelstrom L M, Ahlgren-Tuel L. Dibirdik I, Irvin J D, Langlie M-C, Myers D E. TXU (Anti-CD7)-pokeweed antiviral protein as a potent inhibitor of human immunodeficiency virus. Antimicrob Agents Chemother 1998; 42:383–388.
59. Zarling J M, Moran P A, Haffar O, Sias J, Richman D D, Spina C A, Myers D E, Kuebelbeck V, Ledbetter J A, Uckun F M. Inhibition of HIV replication by pokeweed antiviral protein targeted to CD4+ cells by monoclonal antibodies. Nature 1990; 347:92–95.
60. Erice A, Lieler C L, Meyers D E, Sannerund K J, Irvin J D, Balfour H H, Uckun F M. Inhibition of zidovudine (AZT)-sensitive strains of human immunodeficiency virus type 1 by pokeweed antiviral protein targeted to CD4+ cells. Antimicrob Agents Chemother 1993; 37:835–838.
61. Bosworth N, Towers P. Scintillation proximity assay. Nature 1989; 341:167–168.
62. D'Cruz O J, Ghosh P, Uckun F M. Spermicidal activity of metallocene complexes containing vanadium(IV) in humans. Biol Reprod 1998; 58:1515–1526.
63. D'Cruz O J, Ghosh P, Uckun F M. Spermicidal activity of chelated complexes of bis(cyclopentadienyl)vanadium (IV). Mol Hum Reprod 1998; 4:683–693.
64. D'Cruz O J, Dong Y, Uckun F M. Spermicidal activity of oxovanadium(IV) complexes of 1, 10-phenanthroline, 2,2'-bipyridyl, 5'-bromo-2'-hydroxyacetophenone and derivatives. Biol Reprod 1998; 60:435–444.
65. D'Cruz O J, Venkatachalam T K, Uckun F M. Structural requirements for potent spermicidal activity of dual-function aryl phosphate derivative of bromo-methoxy zidovudine (Compound WHI-07). Biol Reprod 2000; 62:37–44.
66. D'Cruz O J, Venkatachalam T K, Zhu Z, Shih M-J, Uckun F M. Aryl phosphate derivatives of bromo-methoxy azidothymidine are dual-function spermicides with potent anti-HIV activity. Biol Reprod 1998; 59: 503–515.
67. D'Cruz O J, Shih M-J, Yiv S H, Chen C L, Uckun F M. Synthesis, characterization and preclinical formulation of a dual-action phenyl phosphate derivative of bromo-methoxy zidovudine (compound WHI-07) with potent anti-HIV and spermicidal activities. Mol Hum Reprod 1999; 5:421–432.
68. D'Cruz O J, Zhu Z, Yiv S H, Chen C-L, Waurzyniak B, Uckun F M. WHI-05, a novel bromo-methoxy substituted phenyl phosphate derivative of zidovudine, is a dual-action spermicide with potent anti-HIV activity. Contraception 1999; 59:319–331.
69. Venkatachalam T K, D'Cruz O J, Uckun F M. Importance of the alanine methyl ester side chain for the biologic activity profile of dual-function phenyl phosphate derivatives of bromo-methoxy zidovudine (PP-BMZ). Antivir Chem Chemother 2000;
70. Jan S T, Shih M-J, Venkatachalam T K, D'Cruz O J, Chen C L, Uckun F M. Synthesis of dual-function (5R, 6R)- and (5S,6S)-bromo-6-methoxy-AZT-5'-(para-bromophenyl methoxyalaninyl phosphate) as novel spermicidal and anti-HIV agents. Antivir Chem Chemother 1999; 10:39–46.

We claim:

1. A method of inhibiting conception in a mammal, comprising contacting mammalian sperm in need of inactivation with an effective spermicidal or sperm-immobilizing amount of a thiourea compound having the formula:

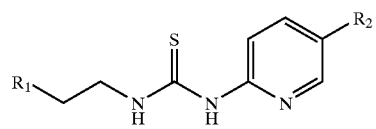

wherein $R_1$ is cyclohexenyl, and $R_2$ is halo or $CF_3$.

2. The method according to claim 1, wherein $R_2$ is halo.
3. The method according to claim 2, wherein $R_2$ is chloro.
4. The method according to claim 2, wherein $R_2$ is bromo.
5. The method according to claim 1, wherein $R_2$ is $CF_3$.
6. A method of inhibiting conception in a mammal, comprising contacting mammalian sperm in need of inactivation with an effective spermicidal or sperm-immobilizing amount of a thiourea compound having the formula:

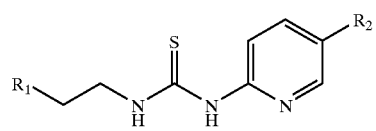

wherein $R_1$ is pyridyl, and $R_2$ is H.

7. A method of inhibiting conception in a mammal, comprising contacting mammalian sperm in need of inactivation with an effective spermicidal or sperm-immobilizing amount of a thiourea compound having the formula:

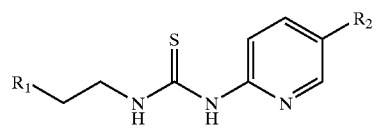

wherein $R_1$ is piperidinyl, and $R_2$ is $CF_3$.

* * * * *